United States Patent
Shibata et al.

(10) Patent No.: US 8,652,049 B2
(45) Date of Patent: Feb. 18, 2014

(54) ULTRASONIC DIAGNOSTIC APPARATUS

(75) Inventors: Chihiro Shibata, Nasushiobara (JP);
Akihiro Kakee, Nasushiobara (JP);
Kenichi Ichioka, Nasushiobara (JP);
Kuramitsu Nishihara, Otawara (JP)

(73) Assignees: Kabushiki Kaisha Toshiba, Tokyo (JP);
Toshiba Medical Systems Corporation, Tochigi-Ken (JP)

( * ) Notice: Subject to any disclaimer, the term of this patent is extended or adjusted under 35 U.S.C. 154(b) by 204 days.

(21) Appl. No.: 13/098,757

(22) Filed: May 2, 2011

(65) Prior Publication Data

US 2011/0282204 A1 Nov. 17, 2011

(30) Foreign Application Priority Data

May 12, 2010 (JP) ................................. 2010-110423

(51) Int. Cl.
*A61B 8/00* (2006.01)
(52) U.S. Cl.
USPC ............................ 600/443; 600/454; 600/441
(58) Field of Classification Search
USPC ........................................................ 600/443
See application file for complete search history.

(56) References Cited

U.S. PATENT DOCUMENTS

| 5,183,047 A | 2/1993 | Burckhardt |
| 5,462,058 A | 10/1995 | Yamada et al. |
| 5,623,928 A | 4/1997 | Wright et al. |
| 5,891,036 A * | 4/1999 | Izumi ............................ 600/441 |
| 2005/0168719 A1* | 8/2005 | Stierle et al. .................. 356/4.01 |
| 2009/0054769 A1* | 2/2009 | Satoh ............................. 600/437 |
| 2010/0280386 A1* | 11/2010 | Bae et al. ....................... 600/454 |

FOREIGN PATENT DOCUMENTS

| JP | 2002-224107 A | | 8/2002 | |
| WO | WO 2010/086216 | * | 8/2010 | ............... H04B 1/66 |

OTHER PUBLICATIONS

EP Extended European Search Report for corresponding EP Application No. 11165717.7 mailed on Sep. 22, 2011.

* cited by examiner

*Primary Examiner* — Tse Chen
*Assistant Examiner* — Patricia Park
(74) *Attorney, Agent, or Firm* — Yoshida & Associates, LLC (57) ABSTRACT

According to one embodiment, an ultrasonic diagnostic apparatus comprises an ultrasonic probe, an ultrasonic transmission/reception unit, an echo processing unit configured to generate complex data based on the echo signals, a phase shifting unit configured to shift a phase of each ensemble data constituted by N complex data associated with the same depth on the same ultrasonic raster in accordance with a reference phase, an interpolation processing unit configured to interpolate ensemble data associated with an interpolated raster between adjacent ultrasonic rasters based on the phase-shifted ensemble data, and an image data generation unit configured to generate image data based on the phase-shifted ensemble data and the interpolated ensemble data.

27 Claims, 8 Drawing Sheets

ULTRASONIC DIAGNOSTIC APPARATUS

CROSS-REFERENCE TO RELATED APPLICATIONS

This application is based upon and claims the benefit of priority from Japanese Patent Application, No. 2010-110423, filed May 12, 2010; the entire contents of which are incorporated herein by reference.

FIELD

Embodiments described herein relate generally to an ultrasonic diagnostic apparatus.

BACKGROUND

In so-called color Doppler imaging which generates a spatial distribution associated with the moving velocity of a moving object such as a blood flow, it is necessary to repeat ultrasonic transmission/reception a plurality of numbers of times in the same ultrasonic raster (to be simply referred to as raster hereinafter) direction. For this reason, when trying to secure a certain number of frames per second (frame rate), it is not possible to obtain a sufficiently large number of rasters. There is a tradeoff relationship between frame rates (time resolutions) and the numbers of rasters (spatial resolutions).

Figure 6:
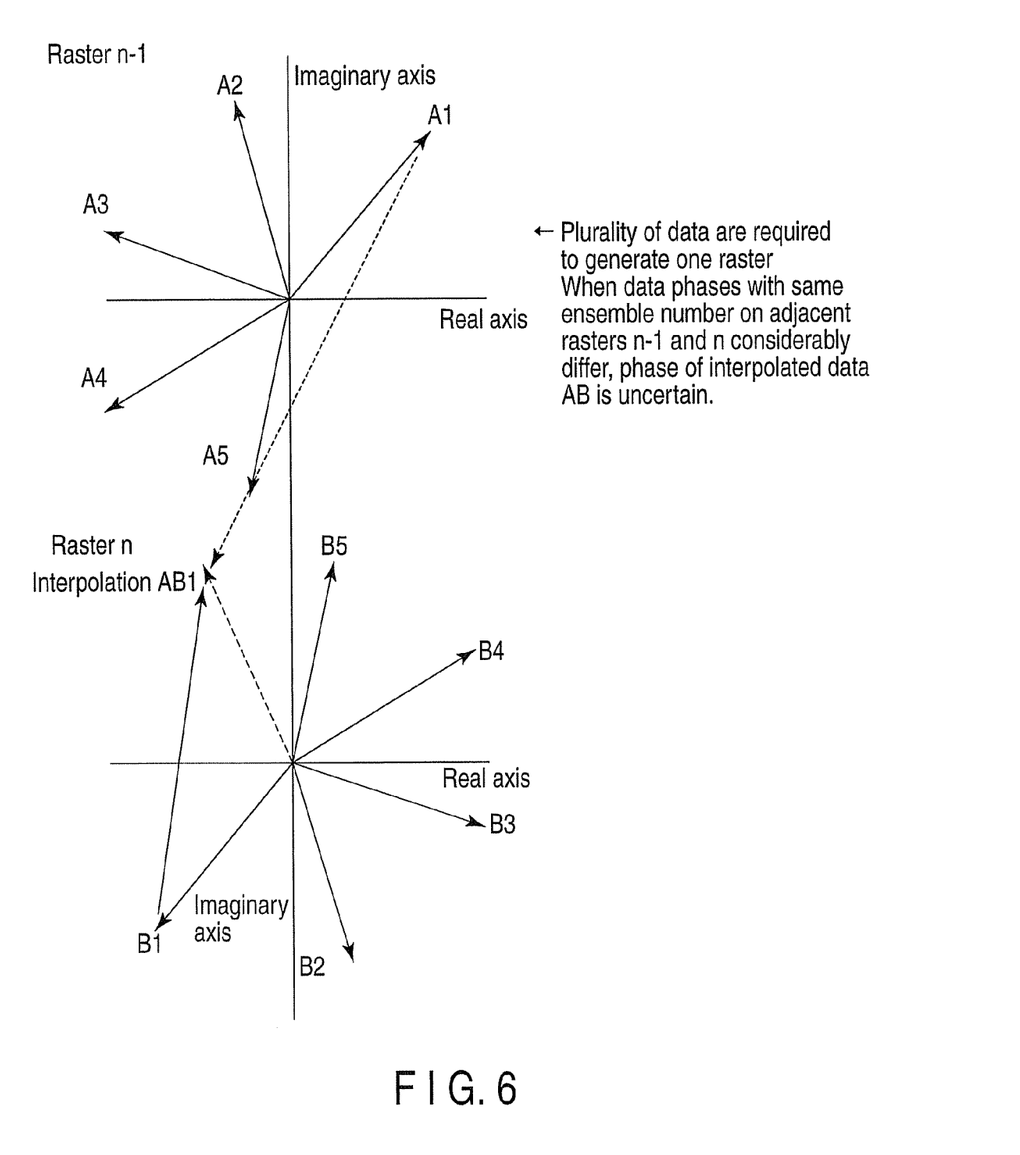
FIG. 6 is a view showing a problematic point in conventional interpolation processing.
Figure 7:
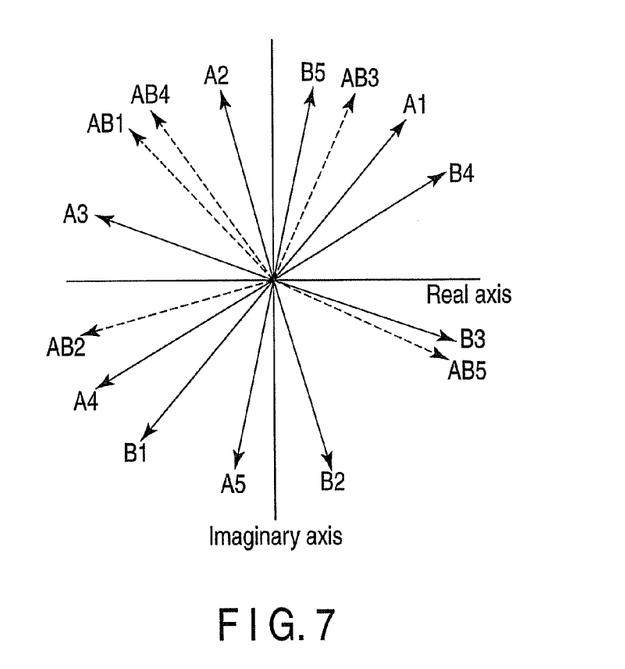
FIG. 7 is a view for explaining conventional interpolation processing.

Raster interpolation is a method of suppressing a degradation in time resolution while maintaining a certain spatial resolution. The mainstream technique of raster interpolation is to directly interpolate the final average velocity of a blood flow or the like. If, however, for example, the pieces of velocity information of adjacent rasters are +α and −α, simply averaging them will result in zero velocity. This may generate an unnatural black part on the interpolated raster. As a method of improving this situation, there is available a raster interpolation method using complex data obtained by quadrature detection, as exemplified by FIGS. 6 and 7. Raster interpolation processing (complex interpolation) on this complex data takes initial amplitudes into consideration. When, therefore, converting the data into an average velocity, it is possible to improve the estimation accuracy of interpolated velocity components.

Figure 8:
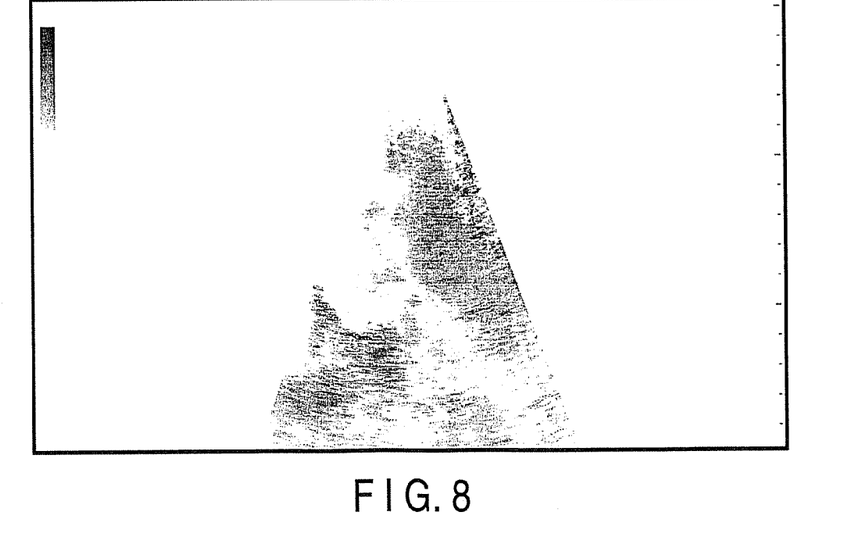
FIG. 8 is a view showing an example of a conventional image.

In complex interpolation, however, a degradation in interpolation accuracy with a velocity change, in particular, appears as an artifact in the form of a vertical streak on the image, as shown in FIG. 8.

DETAILED DESCRIPTION

In general, according to one embodiment, an ultrasonic diagnostic apparatus comprises an ultrasonic probe; an ultrasonic transmission/reception unit configured to repeatedly transmit/receive an ultrasonic wave N times for each of a plurality of ultrasonic rasters via the ultrasonic probe and generate a plurality of echo signals; an echo processing unit configured to generate complex data based on the echo signals; a phase shifting unit configured to shift a phase of each ensemble data constituted by N complex data associated with the same depth on the same ultrasonic raster in accordance with a reference phase; an interpolation processing unit configured to interpolate ensemble data associated with an interpolated raster between adjacent ultrasonic rasters based on the phase-shifted ensemble data; and an image data generation unit configured to generate image data based on the phase-shifted ensemble data and the interpolated ensemble data.

An ultrasonic diagnostic apparatus according to this embodiment will be described below with reference to the views of the accompanying drawing.

Figure 9:
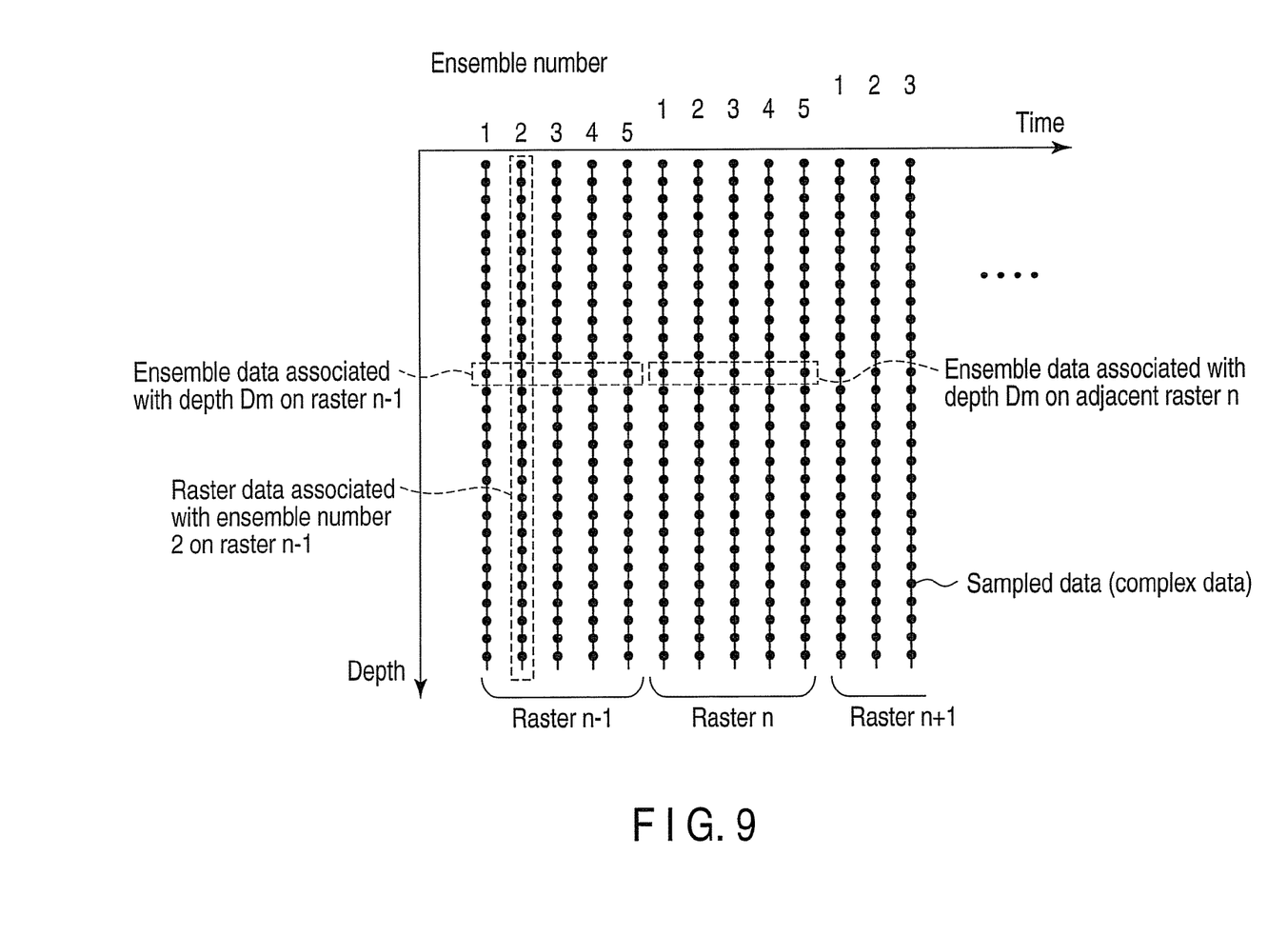
FIG. 9 is a view showing output data from a memory 42 in FIG. 2.

Note that in color Doppler imaging, ultrasonic waves are repetitively transmitted and received N times each at a predetermined repetition period (1/PRF) for each ultrasonic raster (to be simply referred to as a raster hereinafter). In this case, N is defined as the number of ensembles. Referring to FIG. 9, N=5. An echo signal corresponding to each transmission/reception is quadrature-detected and repetitively sampled at a predetermined sampling period. Data at each depth (sampling point) obtained by this sampling operation will be referred to as sampled data. Sampled data is used as complex data constituted by real and imaginary parts. A complex data string in the depth direction associated with the same raster obtained by one transmission/reception is called "raster data". A data string constituted by N complex data in the time direction associated with the same depth on the same raster is called "ensemble data". Transmitting/receiving operations repeated for the same raster are differentiated by ensemble numbers.

An outline of a procedure for image generation processing according to this embodiment will be described first. Note that this image generation processing may be provided as a computer-readable storage medium which records program codes for causing a computer to implement means 1) to 5) described below:

1) the means for specifying the phase difference between a reference phase (e.g., 0°) and one of the phases of N sampled data constituting ensemble data associated with a given depth on a given raster;

2) the means for phase-shifting each of all the N sampled data constituting the ensemble data by the specified phase difference, making the phase of the sampled data used for specifying phase difference become 0°, and maintaining the phase difference between the sampled data used for specifying phase difference and each of the remaining (N−1) sample data at the phase difference before the phase shift processing;

3) the means for executing the processing of 1) and the processing of 2) for all the ensemble data;

4) the means for calculating interpolated values for sample data on adjacent rasters with sample data with the same ensemble number at the same depth, and generating ensemble data (interpolated data) for each depth on the interpolated raster; and 5) the means for calculating movement information such as the average velocity of a blood flow or another moving object by performing autocorrelation processing for actually measured ensemble data and interpolated ensemble data for each depth on the actually measured raster and interpolated raster, and generating a color Doppler image.

As described above, in order to obtain Doppler information, it is a mainstream to use the autocorrelation method. To use this autocorrelation method, it is necessary to perform transmission/reception a plurality of numbers of times (N times) per raster to acquire a plurality of raster data. Using the autocorrelation method will obtain phase information used for velocity display. This embodiment is based on the assumption that autocorrelation processing is performed, and interpolation can be done on complex data by quadrature detection. Assume that in the following description, the number of ensembles is five, sampled data with the ensemble number "1" is the oldest data among the five sampled data constituting ensemble data, and sampled data with the ensemble number "5" is the newest data among five sampled data constituting the ensemble data. Although the reference phase is 0°, it is not limited to this, and may be any value as long as it is constant in phase correction processing.

In addition, sampled data which specifies a phase difference from the reference phase may be any of five sampled data constituting ensemble data including the sampled data specifying the phase difference. In this case, the sampled data located in the middle is used as sampled data specifying a phase difference. According to the following description, ensemble data associated with one middle raster between the (n−1)th raster and the nth raster is interpolated based on ensemble data associated with the (n−1)th raster and ensemble data associated with the nth raster. However, it is possible to interpolate a plurality of rasters between the (n−1)th raster and the nth raster.

Figure 1:
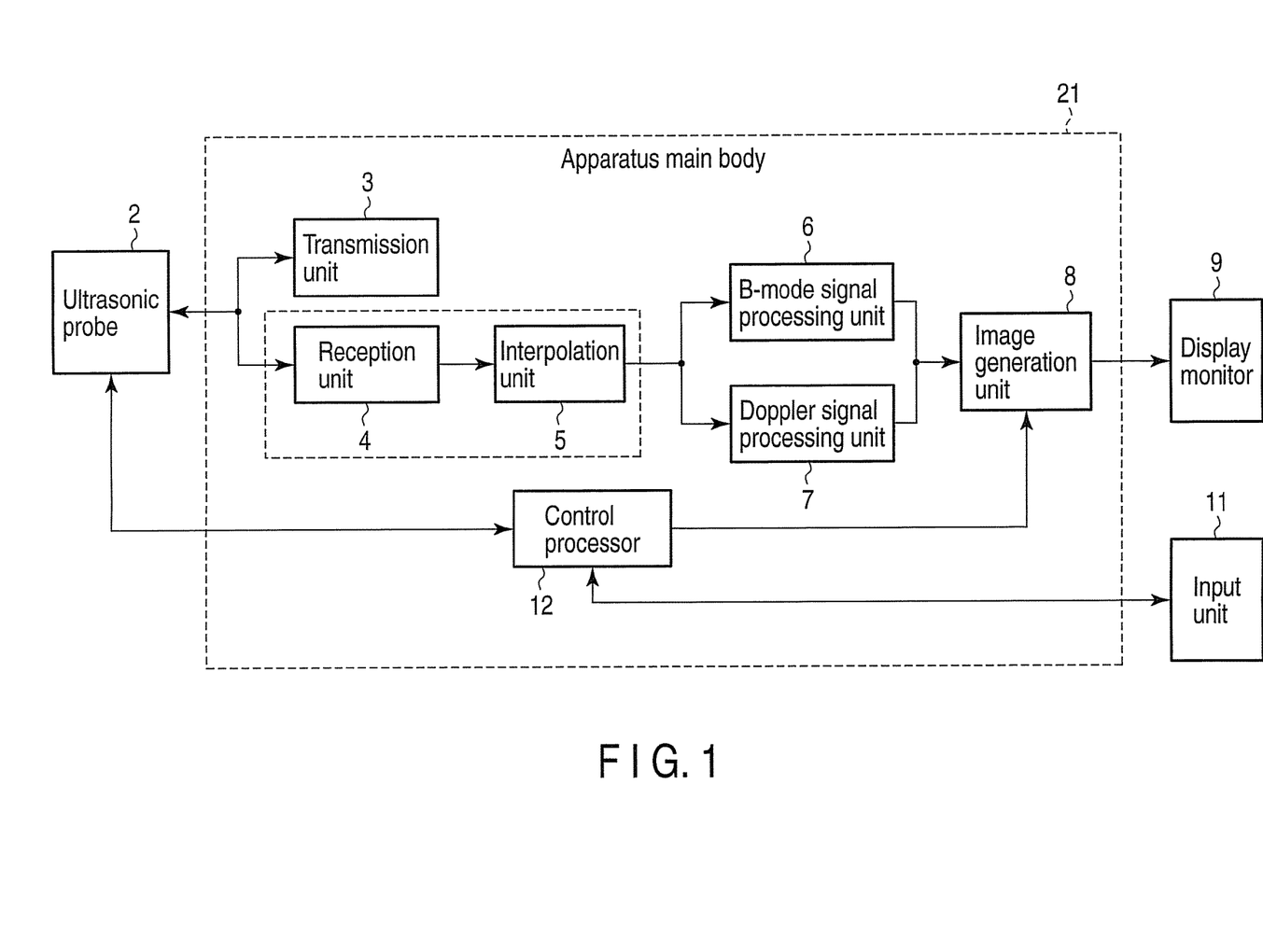
FIG. 1 is a block diagram showing the arrangement of an ultrasonic diagnostic apparatus according to this embodiment.

As shown in FIG. 1, the ultrasonic diagnostic apparatus according to this embodiment includes an ultrasonic probe 2. The ultrasonic probe 2 is of a multi-channel type including a plurality of transducers arrayed in a line. Each transducer is constituted by a piezoelectric element, an individual electrode formed on the upper surface of the piezoelectric element, and a common electrode formed on the lower surface of the piezoelectric element. One electrically isolated channel is constituted by one transducer or several adjacent transducers. The ultrasonic probe 2 is detachably connected to a connector of an apparatus main body 21 housed in a console case.

The apparatus main body 21 includes a transmission unit 3 and a reception unit 4 which are connected to the ultrasonic probe 2. The transmission unit 3 includes a pulser provided for each channel. The pulsers apply driving signals (high-frequency voltage signals) to the transducers in response to pulse signals as triggers which are generated from a pulse generator at a predetermined period (the reciprocal of a pulse repetition frequency PRF) and delayed for the respective channels by a transmission delay circuit.

The ultrasonic waves generated by the mechanical vibrations of the transducers based on the driving signals propagate through the inside of the object and are reflected by the discontinuity surface of acoustic impedance which is located midway in the object. The reflected ultrasonic waves return as an echo to the ultrasonic probe 2. This echo mechanically vibrates the piezoelectric elements of the ultrasonic probe 2. The preamplifier of the reception unit 4 amplifies the weak electrical signal generated by the vibrations. An analog/digital converter converts the amplified signal into digital data. The reception delay circuit delays the data. The adder then adds the data (phase rectifying addition processing) to generate reception data for which directivity is provided by the echo signal.

Figure 2:
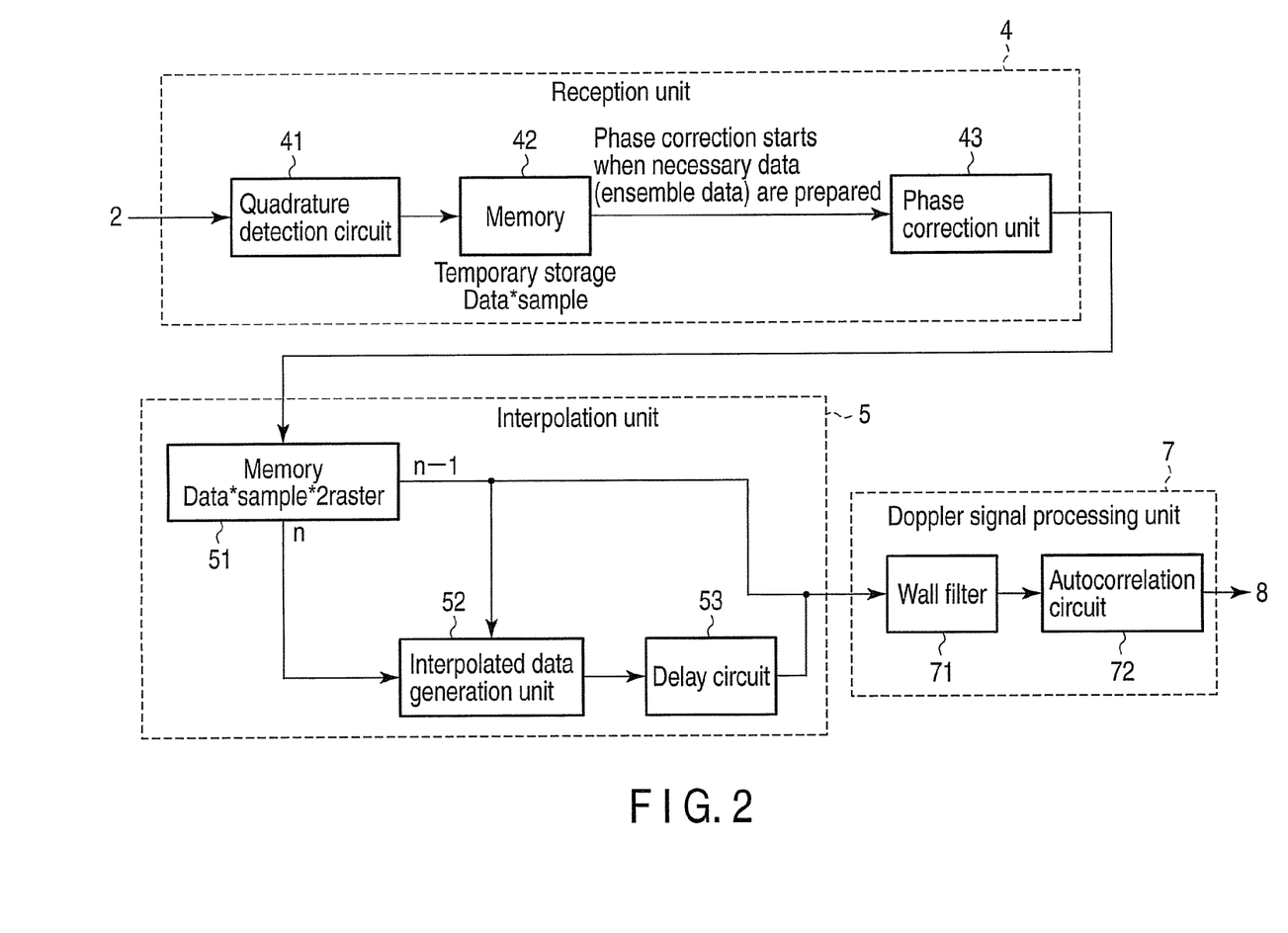
FIG. 2 is a block diagram showing the arrangements of a reception unit and interpolation unit in FIG. 1.

As shown in FIG. 2, a quadrature detection circuit 41 performs quadrature detection processing for the reception data. A memory 42 stores the resultant data as complex data provided with a raster code, depth code, and time code as attributes. In the color Doppler mode, as described above, transmission/reception is performed a plurality of number of times (N times) per raster. When complex data corresponding to the number of ensembles are prepared for each raster and each depth, a phase correction unit 43 reads out N complex data sets, i.e., ensemble data.

The phase correction unit 43 specifies a phase difference relative to the reference phase for each set (ensemble data) of N complex data associated with the same raster and the same depth, and shifts the phases of the N complex data constituting the ensemble data by the specified phase differences. This phase shift (phase correction) processing is performed for each of all the rasters and each of all the depths (sampling points).

Figure 3:
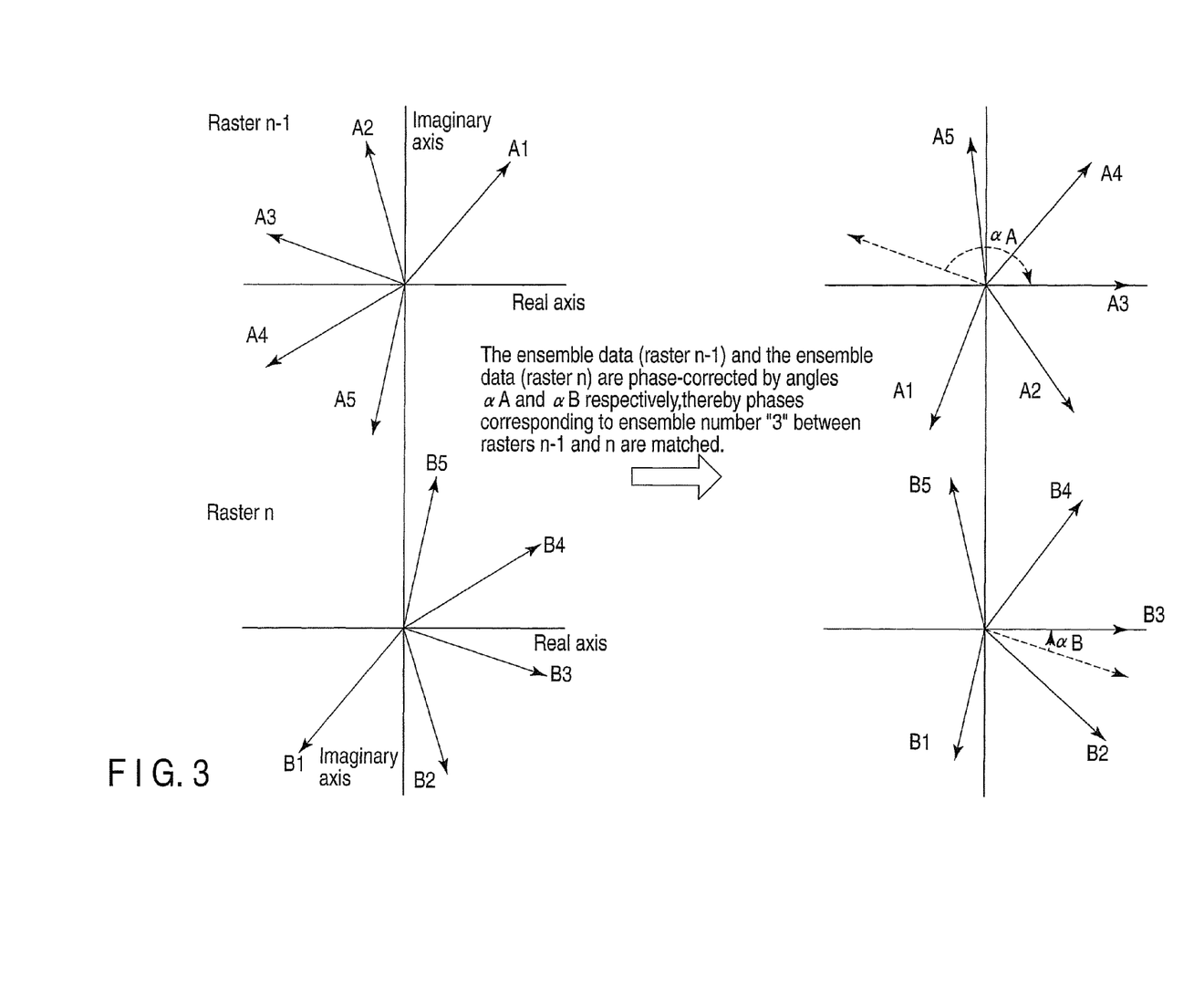
FIG. 3 is a view for explaining phase correction processing by a phase correction unit in FIG. 2.

That is, as shown in FIG. 3, typically, the reference phase is set to 0°, a phase difference $\alpha A$ between the reference phase and the phase of complex data A3 with a predetermined ensemble number (to be referred to as a reference ensemble number) in ensemble data is specified, and each of all the phases of five complex data A1 to A5 constituting the ensemble data is shifted by the specified phase difference $\alpha A$.

If the number of complex data constituting ensemble data is represented by N, it is most effective in terms of reducing artifacts due to phase correction to set the reference ensemble number to (N/2) located in the middle on the time axis. In the case shown in FIG. 3, the reference ensemble number is set to "3".

The phase correction unit 43 shifts the phases of the five complex data A1 to A5 constituting the ensemble data by the same phase angle $\alpha A$ so as to set the phase of the central complex data A3 of the ensemble data to 0°. Note that the operator can arbitrarily change the reference ensemble number and the reference phase via an input unit 11.

Figure 10:
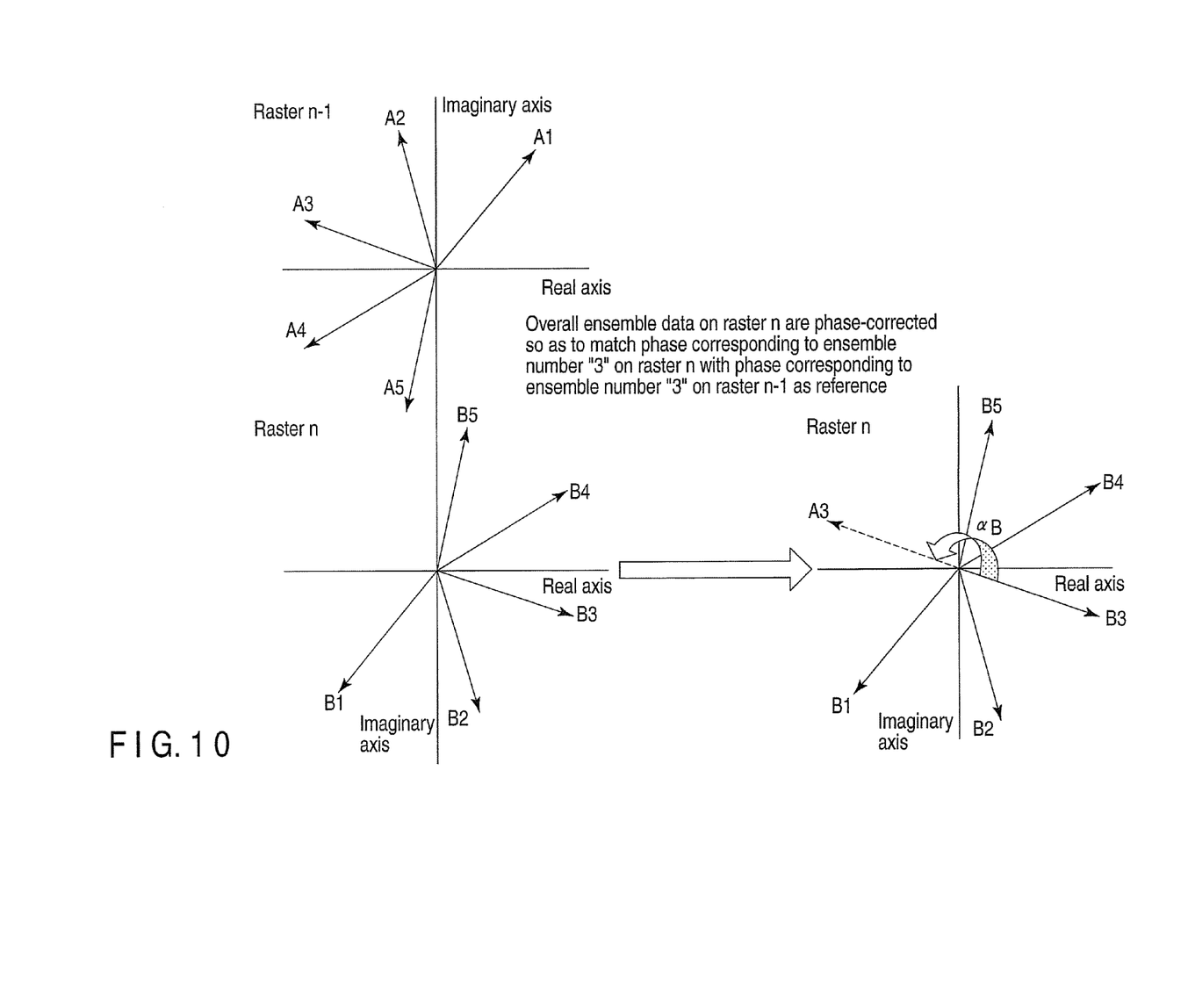
FIG. 10 is a view for explaining another phase correction processing by the phase correction unit in FIG. 2.

Note that, as shown in FIG. 10, it is possible to set, as a reference phase, the phase angle of the complex data with the reference ensemble number "3" on one raster n−1. In this case, when the phase of the complex data with the ensemble number "3" on the raster n is to be corrected to match the phase of the complex data with the ensemble number "3" on the raster n−1, the phase of the complex data with the ensemble number "3" on the raster n is corrected as follows;

complex data (reference) with ensemble number "3" on raster n−1; $a+b*i$ complex data (before correction) with ensemble number "3" on raster n; $c+d*i$ complex data (after correction) with ensemble number "3" on raster n; $(c+d*i)/(a+b*i)*|(a+b*i)|$ Note that in the above case, the number of ensembles is five. Assume however that the number of ensembles is six, an even number, and phase shifting is performed with reference to complex data with a central ensemble number. In this case, it is possible to use a method of generating new reference complex data for phase correction by averaging the complex data with the ensemble number "3" and the complex data with the ensemble number "4", and then shifting the phase of each complex data of ensemble data by the phase difference between the reference complex data and the reference phase.

In this case, the reference phase data is used for only phase correction processing and is not supplied to a Doppler signal processing unit 7.

An interpolation unit 5 includes a memory 51, an interpolated data generation unit 52, and a delay circuit 53. The interpolated data generation unit 52 receives, via the memory 51, ensemble data B1 to B5 associated with the nth raster and phase-corrected by the phase correction unit 43 and ensemble data A1 to A5 associated with the (n−1)th raster adjacent to the nth raster and phase-corrected by the phase correction unit 43.

The interpolated data generation unit 52 generates ensemble data (interpolated ensemble data) associated with one raster (interpolated raster, i.e., ((n+(n−1))/2)th raster) typically located in the middle between two adjacent rasters based on ensemble data (actually measured ensemble data) associated with the two adjacent rasters.

Interpolation of complex data is calculated as follows:
if complex data at depth corresponding to ensemble number 2 on (n−1)th raster; An−1+Bn−1*j, and
complex data at depth corresponding to ensemble number 2 on nth raster; An+Bn*j, then
complex data at the same depth on the interpolated raster is given by (An−1+An)/2+(Bn−1+Bn)*i/2

Although the interpolated data is generated by averaging the complex data of the adjacent rasters, it is possible to use any method.

Figure 4:
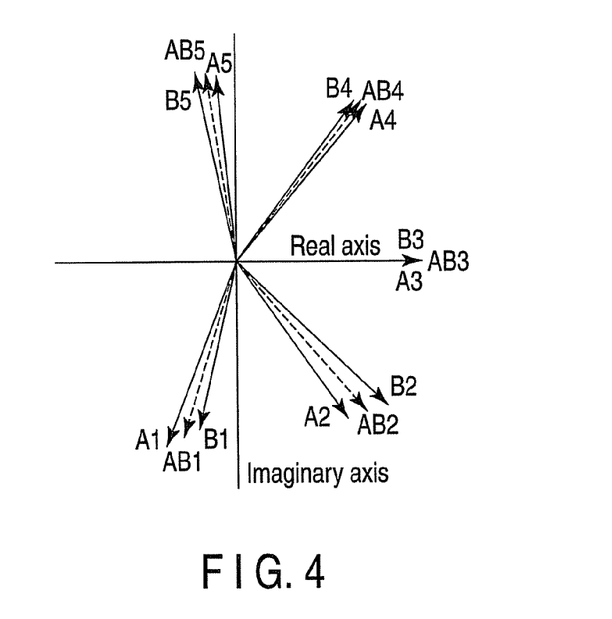
FIG. 4 is a view for explaining interpolation processing by the interpolation unit in FIG. 1.
Figure 5:
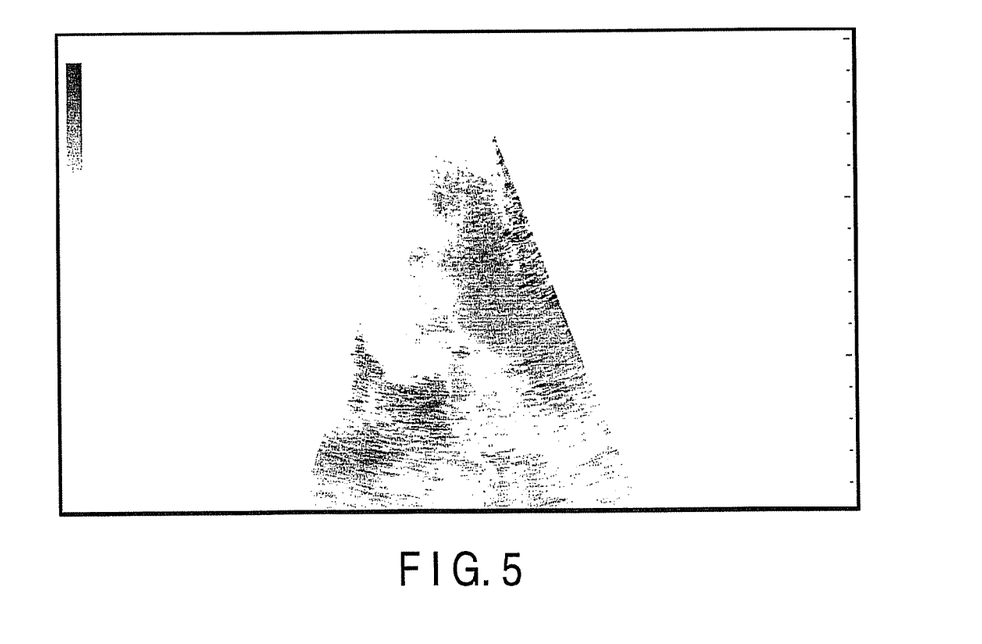
FIG. 5 is a view showing an example of an image according to this embodiment.

Interpolation processing is specifically performed as follows. As shown in FIG. 4, ensemble data AB1 to AB5 on an interpolated raster are generated typically by calculating the average value of complex data with each ensemble number of five complex data constituting actually measured ensemble data at a given depth on the nth raster and complex data of the same ensemble number of actually measured ensemble data at the same depth on the (n−1)th raster. This processing is repeated for all the ensemble numbers, all the depths (sampling points), and all the rasters. This unifies the phases of the complex data with the reference ensemble number to 0° among all the ensemble data. This eliminates or reduces phase shifts between the rasters. This makes it possible to suppress a degradation in interpolation accuracy with velocity changes, in particular, due to complex interpolation, and reduce an artifact in the form of a vertical streak on an image, as shown in FIG. 5, as is obvious from comparison with the image shown in FIG. 8. In addition, interpolation increases the number of rasters, and hence can improve the spatial resolution about twice while maintaining the time resolution.

The interpolated data generation unit 52 outputs the raster data of the interpolated raster (the complex data set on the interpolated raster) after the (n−1)th actually measured raster data and before the nth actually measured raster data via the delay circuit 53.

The Doppler signal processing unit 7 includes a wall filter 71 and an autocorrelation circuit 72. The wall filter 71 passes only high-frequency components (blood flow components), of phase-corrected raster data, which have undergone frequency shifts due to reflection mainly by fast moving objects such as blood cells, and removes low-frequency components (clutter components) having undergone frequency shifts due to reflection mainly by slow moving objects such as the cardiac wall. The autocorrelation circuit 72 obtains velocity information (average velocity, variance, and power), by autocorrelation processing, from the raster data from which clutter components are removed by the wall filter 71.

An image generation unit 8 converts the obtained blood flow information into information based on the TV scanning system, and also converts it into an analog signal to be displayed as an average velocity image, a variance image, a power image, or an image based on an arbitrary combination of them, in color, on a display monitor 9 in accordance with an instruction issued by the operator via the input unit 11.

Note that this apparatus also includes a B-mode signal processing unit 6. The B-mode signal processing unit 6 includes a detection circuit, logarithmic amplifier, and analog/digital converter. The B-mode signal processing unit 6 detects raster data phase-corrected on complex data or reception data having undergone reception delay and addition without undergoing phase correction, logarithmically amplifies the data, and generates image data reflecting the form of the tissue. This image data is displayed as a halftone image on the display monitor 9 via the image generation unit 8.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe;
an ultrasonic transmission/reception unit configured to repeatedly transmit/receive an ultrasonic wave N times for each of a plurality of ultrasonic rasters via the ultrasonic probe and generate a plurality of echo signals;
an echo processing unit configured to generate complex data based on the echo signals;
a phase shifting unit configured to shift a phase of each ensemble data constituted by N complex data associated with the same depth on the same ultrasonic raster in accordance with a reference phase;
an interpolation processing unit configured to interpolate ensemble data associated with an interpolated raster between adjacent ultrasonic rasters based on the phase-shifted ensemble data; and
an image data generation unit configured to generate image data based on the phase-shifted ensemble data and the interpolated ensemble data, wherein the phase shifting unit specifies an average of a phase difference between a phase of N/2th complex data of the ensemble data and the reference phase and a phase difference between a phase of ((N/2)+1)th complex data and the reference phase when the number N is an even number.

2. The apparatus according to claim 1, wherein the interpolation processing unit calculates a real part average and imaginary part average of ensemble data associated with the adjacent ultrasonic rasters.

3. The apparatus according to claim 1, wherein the image data generation unit generates image data associated with movement information of a blood flow or another moving object by performing autocorrelation processing for the ensemble data.

4. The apparatus according to claim 1, wherein the phase shifting unit specifies a phase difference between a phase of ((N+1)/2)th complex data of the ensemble data and the reference phase when the number N is an odd number.

5. The apparatus according to claim 4, wherein the phase shifting unit shifts phases of N complex data constituting the ensemble data in accordance with the phase difference.

6. An ultrasonic diagnostic apparatus comprising:
an ultrasonic probe;
an ultrasonic transmission/reception unit configured to repeatedly transmit/receive an ultrasonic wave N times for each of a plurality of ultrasonic rasters via the ultrasonic probe and generate a plurality of echo signals;
an echo processing unit configured to generate complex data based on the echo signals;
a phase shifting unit configured to shift a phase of each ensemble data constituted by N complex data associated with the same depth on the same ultrasonic raster in accordance with a reference phase;
an interpolation processing unit configured to interpolate ensemble data associated with an interpolated raster between adjacent ultrasonic rasters based on the phase-shifted ensemble data; and
an image data generation unit configured to generate image data based on the phase-shifted ensemble data and the interpolated ensemble data,
wherein the phase shifting unit specifies an average of a phase difference between a phase of N/2th complex data of the ensemble data and the reference phase and a phase difference between a phase of ((N/2)+1)th complex data and the reference phase when the number N is an even number, wherein the phase shifting unit shifts phases of the N complex data constituting the ensemble data in accordance with the average of the phase differences.

7. The apparatus according to claim 1, wherein the reference phase is set to 0°.

8. The apparatus according to claim 1, wherein the reference phase is set to a phase angle of any of complex data constituting ensemble data associated with one of the adjacent ultrasonic rasters.

9. The apparatus according to claim 1, wherein the reference phase is set to a phase angle of complex data, of N complex data constituting ensemble data associated with one of the adjacent ultrasonic rasters, which is located in the middle on a time axis.

10. A non-transitory computer-readable storage medium recording a program code for causing a computer to implement
signal storage means for storing a plurality of echo signals, the plurality of echo signals being generated by repeatedly transmitting/receiving an ultrasonic wave N times for each of a plurality of ultrasonic rasters,
data generation means for generating complex data based on the echo signals,
phase shifting means for shifting a phase of each ensemble data constituted by N complex data associated with the same depth on the same ultrasonic raster in accordance with a reference phase,
interpolation processing means for interpolating ensemble data associated with an interpolated raster between adjacent ultrasonic rasters based on the phase-shifted ensemble data, and
image data generation means for generating image data based on the phase-shifted ensemble data and the interpolated ensemble data, wherein the phase shifting means specifies an average of a phase difference between a phase of N/2th complex data of the ensemble data and the reference phase and a phase difference between a phase of ((N/2)+1)th complex data and the reference phase when the number N is an even number.

11. The non-transitory medium according to claim 10, wherein the interpolation processing means calculates a real part average and imaginary part average of ensemble data associated with the adjacent ultrasonic rasters.

12. The non-transitory medium according to claim 10, wherein the image data generation means generates image data associated with movement information of a blood flow or another moving object by performing autocorrelation processing for the ensemble data.

13. The non-transitory medium according to claim 10, wherein the phase shifting means specifies a phase difference between a phase of ((N+1)/2)th complex data of the ensemble data and the reference phase when the number N is an odd number.

14. The non-transitory medium according to claim 13, wherein the phase shifting means shifts phases of N complex data constituting the ensemble data in accordance with the phase difference.

15. A non-transitory computer-readable storage medium recording a program code for causing a computer to implement
signal storage means for storing a plurality of echo signals, the plurality of echo signals being generated by repeatedly transmitting/receiving an ultrasonic wave N times for each of a plurality of ultrasonic rasters,
data generation means for generating complex data based on the echo signals,
phase shifting means for shifting a phase of each ensemble data constituted by N complex data associated with the same depth on the same ultrasonic raster in accordance with a reference phase,
interpolation processing means for interpolating ensemble data associated with an interpolated raster between adjacent ultrasonic rasters based on the phase-shifted ensemble data, and
image data generation means for generating image data based on the phase-shifted ensemble data and the interpolated ensemble data, wherein the phase shifting means specifies an average of a phase difference between a phase of N/2th complex data of the ensemble data and the reference phase and a phase difference between a phase of ((N/2)+1)th complex data and the reference phase when the number N is an even number, wherein the phase shifting means shifts phases of the N complex data constituting the ensemble data in accordance with the average of the phase differences.

16. The non-transitory medium according to claim 10, wherein the reference phase is set to 0°.

17. The non-transitory medium according to claim 10, wherein the reference phase is set to a phase angle of any of complex data constituting ensemble data associated with one of the adjacent ultrasonic rasters.

18. The non-transitory medium according to claim 10, wherein the reference phase is set to a phase angle of complex data, of N complex data constituting ensemble data associated with one of the adjacent ultrasonic rasters, which is located in the middle on a time axis.

19. The apparatus according to claim 6, wherein the image data generation unit generates image data associated with movement information of a blood flow or another moving object by performing autocorrelation processing for the ensemble data.

20. The apparatus according to claim 6, wherein the phase shifting unit specifies a phase difference between a phase of ((N+1)/2)th complex data of the ensemble data and the reference phase when the number N is an odd number.

21. The apparatus according to claim 20, wherein the phase shifting unit shifts phases of N complex data constituting the ensemble data in accordance with the phase difference.

22. The apparatus according to claim 6, wherein the reference phase is set to 0°.

23. The apparatus according to claim 6, wherein the reference phase is set to a phase angle of any of complex data constituting ensemble data associated with one of the adjacent ultrasonic rasters.

24. The apparatus according to claim 6, wherein the reference phase is set to a phase angle of complex data, of N complex data constituting ensemble data associated with one of the adjacent ultrasonic rasters, which is located in the middle on a time axis.

25. The non-transitory medium according to claim 15, wherein the reference phase is set to 0°.

26. The non-transitory medium according to claim 15, wherein the reference phase is set to a phase angle of any of complex data constituting ensemble data associated with one of the adjacent ultrasonic rasters.

27. The non-transitory medium according to claim 15, wherein the reference phase is set to a phase angle of complex data, of N complex data constituting ensemble data associated with one of the adjacent ultrasonic rasters, which is located in the middle on a time axis.

* * * * *